(12) United States Patent
Mihashi (10) Patent No.: US 6,899,428 B2
(45) Date of Patent: May 31, 2005

(54) CONTRAST SENSITIVITY MEASURING DEVICE AND CONTRAST SENSITIVITY MEASURING METHOD

(75) Inventor: Toshifumi Mihashi, Tokyo (JP)

(73) Assignee: Topcon Corporation, Tokyo (JP)

( * ) Notice: Subject to any disclaimer, the term of this patent is extended or adjusted under 35 U.S.C. 154(b) by 330 days.

(21) Appl. No.: 10/337,409

(22) Filed: Jan. 7, 2003

(65) Prior Publication Data

US 2003/0147048 A1 Aug. 7, 2003

(51) Int. Cl.⁷ ............................. A61B 3/02; A61B 3/00
(52) U.S. Cl. ...................................... 351/239; 351/246
(58) Field of Search ................................ 351/205, 211, 351/213–215, 221, 222, 237, 239–243, 246

(56) References Cited

U.S. PATENT DOCUMENTS

| 4,511,228 A | 4/1985 | von Gierke et al. |
| 6,213,956 B1 | 4/2001 | Lawton |
| 6,338,559 B1 * | 1/2002 | Williams et al. ............ 351/212 |
| 2003/0164923 A1 * | 9/2003 | Hirohara et al. ............ 351/216 |

OTHER PUBLICATIONS

N. Maeda et al., "Correlations Between Visual Functions and Higher–Order Aberrations Measured with Hartmann–Shack Sensor", IOVS, vol. 42, No. 4, Annual Meeting of the Association for Research in Vision and Ophthalmology, Apr. 29–May 4, 2001, p. S897.

N. Maeda et al., "Prediction of Letter Contrast Sensitivity Using Videokeratographic Indices", American Journal of Ophthalmology, vol. 129, No. 6, Jun. 2000, pp. 759–763.

P. de la Villa et al., "A Computer–Driven Optical System for Light Stimulation in Physiological Experiments on Retinal Cells", Measurements Science and Technology, vol. 6, No. 1, Jan. 6, 1995, pp. 67–71.

A. Ginsburg et al., "Quantification of Visual Capability", The Perception of Visual Information, Second Edition, Mar. 1997, the index and pp. 57–86.

* cited by examiner

Primary Examiner—Brian L. Casler
Assistant Examiner—John R. Sanders
(74) Attorney, Agent, or Firm—Foley & Lardner LLP

(57) ABSTRACT

The present invention relates to a device and methods for contrast sensitivity measurement. The device and the methods make it possible to precisely measure the contrast sensitivity of a subject within a short period of time. The device comprises a contrast target display part 100 for displaying contrast targets for a contrast sensitivity test, a contrast target data determination part 320 for determining contrast targets to be displayed on the contrast target display part 100 according to data on optical characteristics of an eye of a subject to be examined, a contrast target display control part 330 for instructing the contrast target display part 100 to display contrast targets based on contrast target data created in the contrast target data determination part 320 according to a predetermined procedure, and a display part 600 for displaying the results of contrast measurement of the subject using data on a history of responses of the subject to displayed contrast targets.

18 Claims, 11 Drawing Sheets

CONTRAST SENSITIVITY MEASURING DEVICE AND CONTRAST SENSITIVITY MEASURING METHOD

BACKGROUND OF INVENTION

The present invention relates to a contrast sensitivity measuring device suitable for use in a visual acuity test using a contrast chart. More specifically, the present invention relates to a contrast sensitivity measuring device and a contrast sensitivity measuring method suitable for precisely determining the ocular aberration of a subject at the time of a laser optical surgery or improvement of visual acuity with glasses or contact lenses.

In recent years, optical surgeries by which the shapes of corneas are altered with laser are attempted. At the time of such surgeries, it is important to precisely measure the ocular aberration. Before and after a cornea surgery or a cataract surgery, visual function tests, including measurement of visual acuity, a low-contrast visual acuity test (which is also referred to as "contrast visual acuity test") and a contrast sensitivity test are performed.

Here, a general visual acuity test using a standard visual acuity chart measures the visual acuity to a minute object with a high contrast ratio. Then, in a cataract patient, for example, turbidity of a lens causes scatter of light, which lowers the contrast of an image on the fundus but does not affect deviation of the optical focus position of the image. As a result, the cataract patient as a subject may be able to read the image as a letter although the image on the fundus is blur. Also in the case where a spherical aberration is caused by optical distortion of a cornea and a lens, the subject may be able to read the image as a letter although the image on the fundus is blur.

Contrast sensitivity which represents the ability to detect a specific object with a minimum contrast is an important index to express the visual ability of a subject in daily and social life. Thus, in measurement of contrast sensitivity, a sine wave grid pattern is used to examine a single modulation transfer function. A sine wave grid pattern is a grid pattern in which the density is changed in a sine wave pattern. In a contrast sensitivity test, the minimum contrast necessary to recognize the grid pattern is measured at various finenesses (spatial frequencies).

However, since contrast sensitivity is measured in such a manner that a subject reads a visual acuity chart under an examiner's direction, there are the following problems.

(1) As the test is performed using a single visual acuity chart, the subject remembers the visual acuity chart when the test is repeated. For example, when the left eye is examined after the right eye and when the right eye is better than the left eye, the subject can respond correctly with memory even if it cannot see with the left eye. Thus, it is difficult to measure the contrast sensitivity of a subject precisely.

(2) It takes about 10 minutes to measure contrast sensitivity and a clinical technologist or ophthalmologist must concentrate on the test during that time. Thus, the practice time or the examination time is unavoidably long.

SUMMARY OF THE INVENTION

The present invention has been made to solve the above problems, and it is, therefore, an object of the present invention to provide a contrast sensitivity measuring device and a contrast sensitivity measuring method which can measure the contrast sensitivity of a subject precisely within a short period of time.

Figure 1:
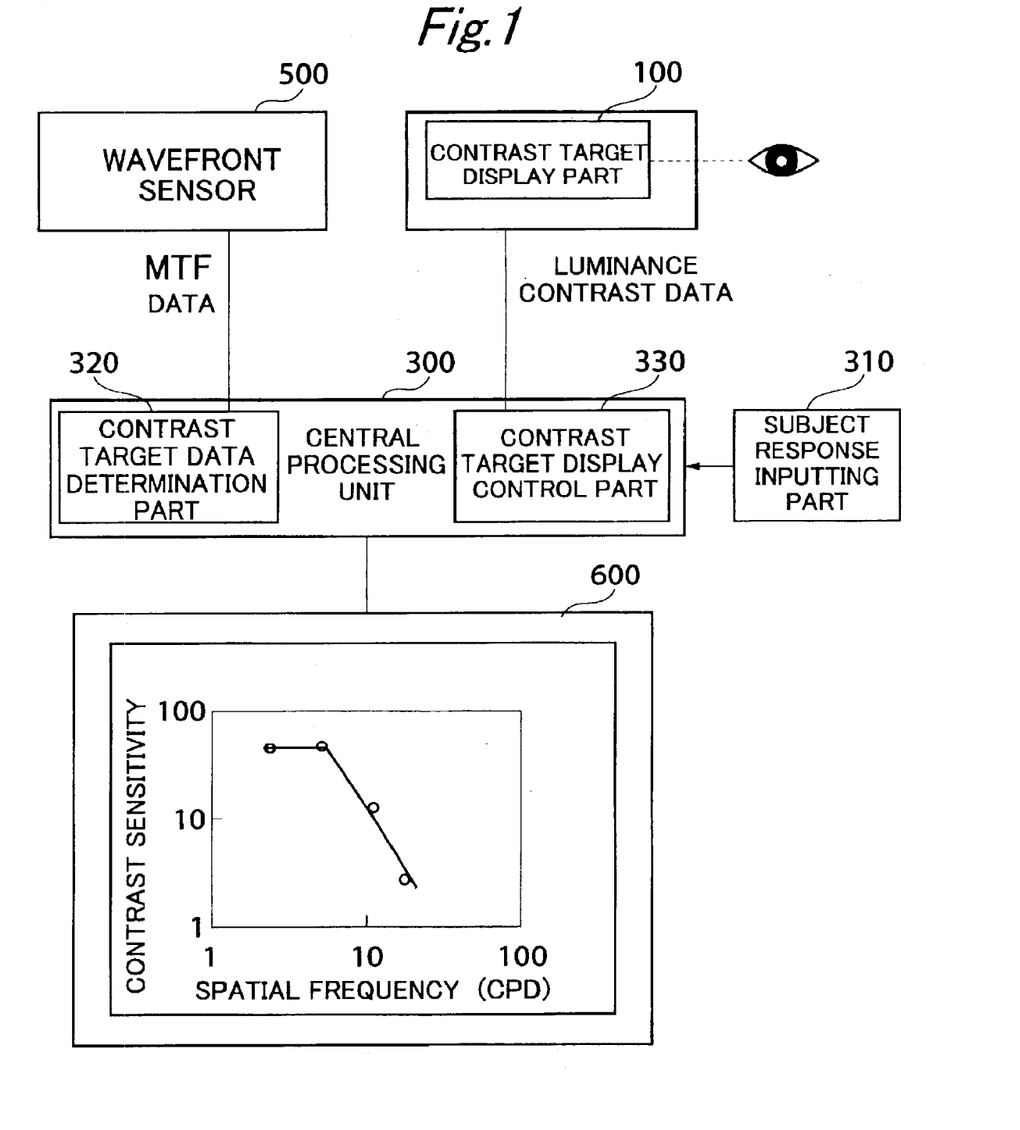
FIG. 1 is a block diagram for explaining a first embodiment of the present invention.

In accomplishing the above object, a contrast sensitivity measuring device of the present invention comprises, as shown in FIG. 1, a contrast target display part 100 for displaying contrast targets for a contrast sensitivity test, a contrast target data determination part 320 for determining contrast targets to be displayed on the contrast target display part 100 according to data on optical characteristics of an eye of a subject to be examined, a contrast target display control part 330 for instructing the contrast target display part 100 to display contrast targets based on contrast target data created in the contrast target data determination part 320 according to a predetermined procedure, and a display part 600 for displaying the results of contrast measurement of the subject using data on a history of responses of the subject to displayed contrast targets.

In a device constituted as above, since the contrast targets to be displayed on the contrast target display part 100 are determined by the contrast target determination part 320 based on the data on optical characteristics of the eye of the subject to be examined, the contrast sensitivity of the eye to be examined can be rapidly measured. Also, since the contrast target control part 330 instructs the contrast target display part 100 to display contrast targets based on contrast target data created in the contrast target data determination part 320 according to a predetermined procedure, the display of the contrast targets can be automated. Thus, the clinical technologist or ophthalmologist can concentrate on checking whether anything out of the ordinary takes place in the subject during the contrast sensitivity test. Since the display part 600 displays the results of the contrast measurement of the subject using data on a history of responses of the subject to displayed contrast targets, the clinical technologist or ophthalmologist can easily judge whether the contrast sensitivity test has been properly performed or not.

Preferably, the contrast target determination part 320 is adapted to determine the contrast targets to be displayed on the contrast target display part 100 based on the results of the contrast measurement which has been already performed on the subject in addition to the data on optical characteristics of the eye to be examined. In this case, a test in the case where the eye to be examined has an average contrast sensitivity can be smoothly performed, so that the time for an examination which is conducted when a lesion is found in the eye can be easily secured.

Preferably, the contrast target determination part 320 is configured to determine at least one of an initial value of the contrast targets to be displayed and a changing rate of the contrast targets to be displayed based on the data on optical characteristics of the eye to be examined. In this case, a test in the case where the eye to be examined has an average contrast sensitivity can be smoothly conducted.

Preferably, the display part 600 is adapted to display the results of the contrast measurement of the subject in which the data on optical characteristics of the subject are reflected in the results. In this case, the clinical technologist or ophthalmologist can easily judge whether the subject has an average contrast sensitivity or whether there is a possibility of a lesion or not by the contrast sensitivity test.

Preferably, the display part 600 is configured to perform, for the reflection of the data on optical characteristics of the subject, at least one of display of a permissive range by which the result of measurement of contrast of the subject can be judged to be normal or not, display of a measurement area corresponding to an abnormal eye with respect to the result of measurement of contrast of the subject, and display of the fact that the result of measurement of contrast of the subject falls out of a permissive range. In this case, the clinical technologist or ophthalmologist can easily judge whether the contrast sensitivity test has been properly performed or not and rapidly perform a retest of the eye when necessary.

Preferably, the data on optical characteristics of the eye to be examined is a modulation transfer function calculated from wavefront information obtained by a wavefront sensor in a spatial frequency region including spatial frequencies displayed on the contrast target display part 100. In this case, the clinical technologist or ophthalmologist can compare the modulation transfer function with the results of the contrast measurement of the subject and judge whether the contrast sensitivity test has been properly performed or not.

Figure 4:
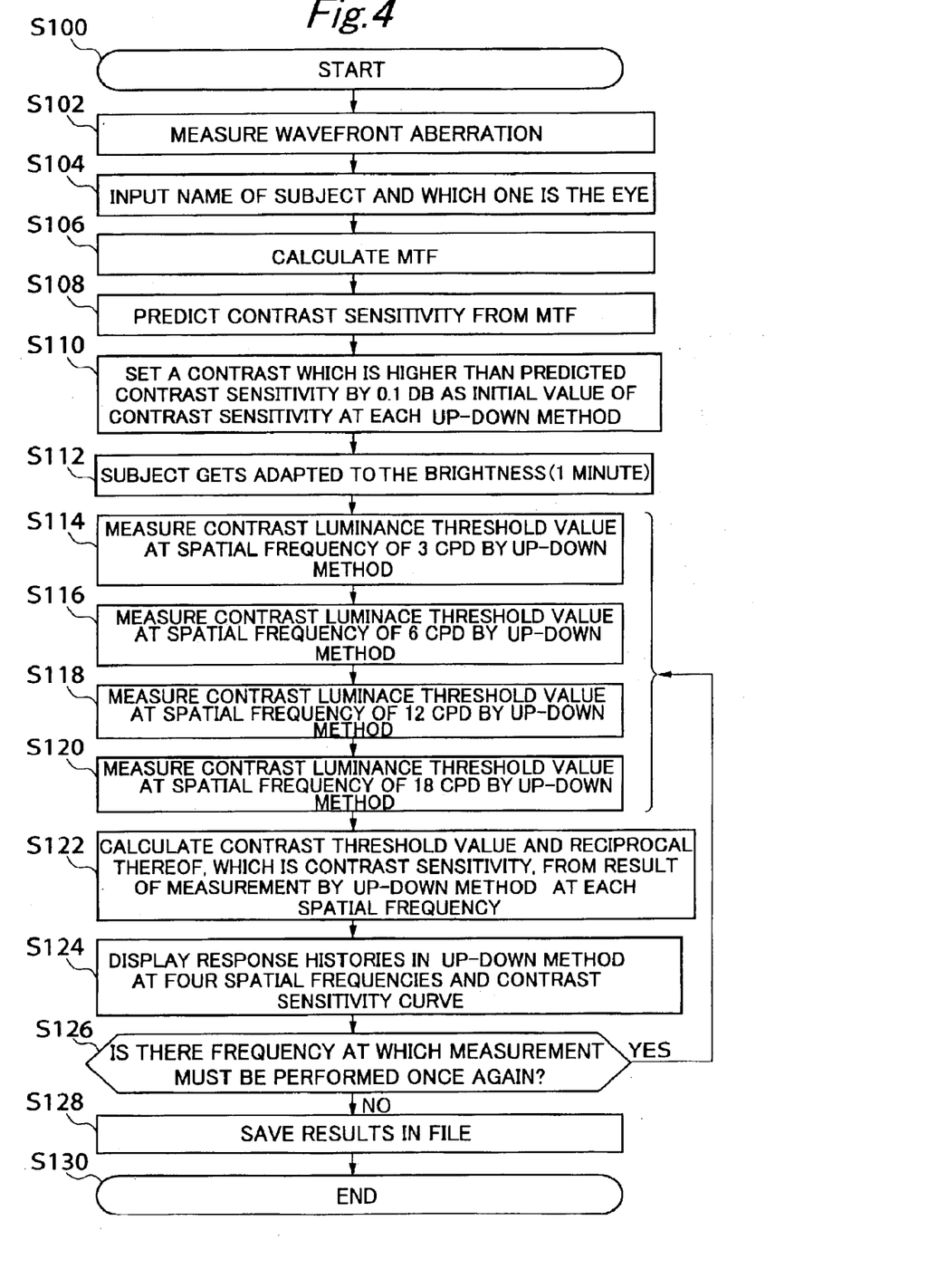
FIG. 4 is a flowchart for explaining a contrast sensitivity test using data on optical characteristics of a subject.

In accomplishing the above object, a contrast sensitivity measuring method of the present invention comprises the steps of, as shown in FIG. 4, determining contrast targets to be displayed on a contrast target display part according to data on optical characteristics of an eye of an subject to be examined (S102 to S110), displaying contrast targets on the contrast target display part based on contrast target data created in a contrast target data determination part according to a predetermined procedure (S114 to S120), and displaying the results of the contrast measurement of the subject using data on a history of responses of the subject to displayed contrast targets (S122 to S124).

This application is based on Japanese patent applications, No.2002-003444 filed in Japan on Jan. 10, 2002, which are entirely incorporated herein by reference.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

BRIEF DESCRIPTION OF THE DRAWINGS

FIG. 5 is views for explaining a stimulus display pattern for use in an up-down method shown in FIG. 4;

DESCRIPTION OF THE PREFERRED EMBODIMENTS

Description will be hereinafter made of the embodiments of the present invention with reference to the drawings. In the drawings, the same or corresponding members are designated by the same or similar numerals, and overlapping descriptions are omitted. FIG. 1 is a block diagram for explaining a first embodiment of the present invention. A contrast target display part 100 is for displaying contrast targets for a contrast sensitivity test, and is described in detail later with reference to FIG. 2.

A central processing unit 300 has a subject response input part 310 such as a mouse, a contrast target data determination part 320 and a contrast target display control part 330, and comprises a computer or a server having a high-speed processor. The contrast target data determination part 320 determines contrast targets to be displayed on the contrast target display part 100 according to data on optical characteristics of an eye to be examined, and sets the contrast sensitivity of the contrast target to be displayed first to a value corresponding to the optical characteristic data of the eye to be examined. The detail of this will be described later with reference to FIG. 10 and FIG. 11.

The contrast target display control part 330 controls the contrast target display part 100 to display contrast targets based on contrast target data created in the contrast target data determination part 320 according to a predetermined procedure. More specifically, the contrast target display control part 330 transmits target display control signals to a test target display control part 120 and a pedestal target display control part 140 as described later.

A wavefront sensor 500 measures the aberration of a cornea or a lens comprising an eyeball of a subject. The main components of the wavefront sensor 500 are an array of small lenses called a small lens array and a camera having an array of sensor elements. This type of wavefront sensor is referred to as "Shack-Hartmann wavefront sensor". The small lens array generates a multiplicity of element portions of light called subapertured portions when placed in a path of a light beam. Each of the lenses of the small lens array processes subapertures of all the light beams. In the small lens array, the lenses are generally arranged in a square lattice, but the array itself may not be square-shaped and usually has a polygonal shape generally matched with the contour of a circular light beam. The sensor elements of the camera generally has a square or rectangular shape and generally arranged in a square or rectangular lattice matched in an angular direction so as to be in parallel with the lattice pattern of the small lenses.

The display part 600 displays the result of measurement of a contrast of the subject using data on a history of responses of the subject to a displayed contrast targets, and comprises, for example, a CRT or a liquid crystal display.

Figure 2:
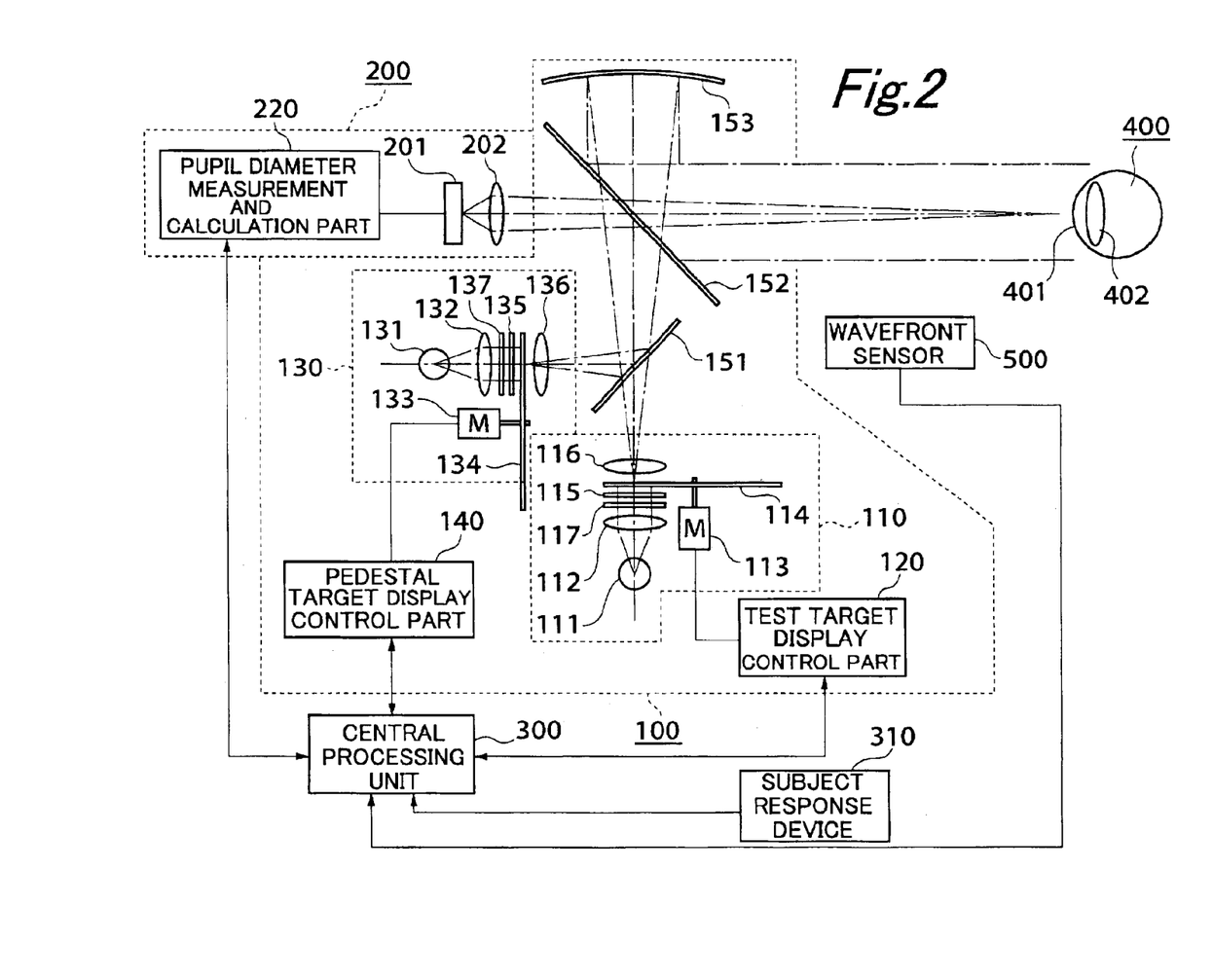
FIG. 2 is a block diagram for explaining in detail a contrast target display part.

FIG. 2 is a block diagram for explaining in detail the contrast target display part, in which an optical system and a control system are shown. As shown in FIG. 2, the contrast target display part 100 comprises a first illumination optical system 110, a test target display control part 120, a second illumination optical system 130 and a pedestal target display control part 140. In FIG. 2, a pupil data measurement part 200, the central processing unit 300 and an eye 400 to be examined of a subject are shown.

The first illumination optical system 110 mainly forms test targets and comprises a light source 111, a condenser lens 112, a target exchanging rotary motor 113, a target plate 114, an ND filter 115, magnification correction lenses 116, and a diffusion plate 117. The condenser lens 112 converts light emitted from the light source 111 into a parallel light beam. On the target plate 114, targets for a contrast sensitivity test suitable for measurement of a modulation transfer function such as a Gabor stimulus and various letters and Landolt rings are printed in predetermined sizes as contrast targets. On contrast sensitivity targets, grid patterns having a spatial frequency of 1.5, 3, 6, 12 and 18 [cycles/deg] at a visual distance of 3 m are drawn.

The ND (Neutral Density) filter 115 is a filter only for changing the quantity of light to, for example, 60% or 40% and does not bring about polarization and soon. The magnification correction lenses 116 have a focal distant of infinity (0 diopter) or 5 m (0.2 diopter). An adjustment is made by exchanging the magnification correction lenses 116 when the test targets are displayed to a subject. The diffusion plate 117 diffuses light coming emitted from the condenser lens 112 to make light quantity distribution uniform.

The second illumination optical system 130 mainly forms a background such as a pedestal target, and comprises a light source 131, a condenser lens 132, a target exchanging rotary motor 133, a target plate 134, an ND filter 135, magnification correction lenses 136, and a diffusion plate 137. The second illumination optical system 130 comprises generally the same types of optical parts as those of the first illumination optical system 110, but different therefrom in that the targets printed on the target plate 134 are backgrounds. On contrast sensitivity targets, test targets each having a specified spatial frequency and a specified contrast are printed. Thus, on the target plate 134 are printed backgrounds to adjust the brightness of all the test targets to be almost the same.

A test target sent from the first illumination optical system 110 and a pedestal target sent from the second illumination optical system 130 are superimposed in a light path by a mirror 151, passed through a spectral mirror 152 as a first mirror, reflected by a concave mirror 153 as a second mirror, reflected by the spectral mirror 152 and reaches an eye anterior segment 401 of a subject. The mirror 151 may be a half mirror. The transmissivity and reflectivity of the mirror 151 may be determined depending upon the quantity of light of the light sources 111 and 131. By properly determining the transmissivity and reflectivity of the mirror 151, energy efficiency can be improved as compared with the case where light is constantly attenuated by the ND filters 115 and 135.

The test target display control part 120 drives the target exchanging rotary motor 113 to move the target plate 114 to a suitable position so that an appropriate test target may be displayed to a subject. The pedestal target display control part 140 drives the target exchanging rotary motor 133 to move the target plate 134 to a suitable position so that a pedestal target having a contrast or brightness corresponding to the test target may be displayed to a subject. The test target display control part 120 and the pedestal target display control part 140 display test targets for specified contrast sensitivites on the contrast target display part 100 according to target display control signals transmitted from the contrast target display control part 330.

The pupil data measurement part 200 comprises a photoreceptor 201, a light detection camera lens system 202, and a pupil diameter measurement and calculation part 220. Since the optical system regarding the targets uses light of a visible wavelength, the pupil data measurement part 200 may use near infrared light or visible light of a wavelength which is different from that of the test targets. For the photoreceptor 201, an element which can receive a planar image such as a charged-coupled device (CCD) is used. The magnification of the camera lens system 202 is adjusted so that an image of a pupil is thrown on the photoreceptor 201 with an optimum magnification. The image of the anterior segment 401 of a subject received by the photoreceptor 201 may include an image of a pupil or pupils. The pupil diameter measurement and calculation part 220 processes and recognizes the image of the anterior segment 401 received by the photoreceptor 201 and outputs the pupil diameter on real time. The area of a pupil region may be used as the pupil data instead of a pupil diameter.

The central processing unit 300 has a function as a measurement timing formation part for generating a timing signal for deciding the timing of the measurement of the pupil diameter of a subject by the pupil data measuring part 200 based on the timing at which the contrast target display part 100 displays a contrast target to the anterior segment 401 of a subject or the timing at which the subject responses. The central processing unit 300 also has a function of combining and processing the information on the contrast displayed by the contrast target display part 100, information on the visual acuity of a subject and the information on the pupil of the subject obtained by the pupil data measurement part 200. The subject response device 310 as a subject response input part is used to input the responses of a subject to the contrast targets and comprises an I/O device such as a mouse. The output signals from the subject response device 310 are inputted into the central processing unit 300.

As anatomically known, an eye 400 to be examined of a subject has the anterior segment 401 including a cornea, and a lens 402.

Figure 3A:
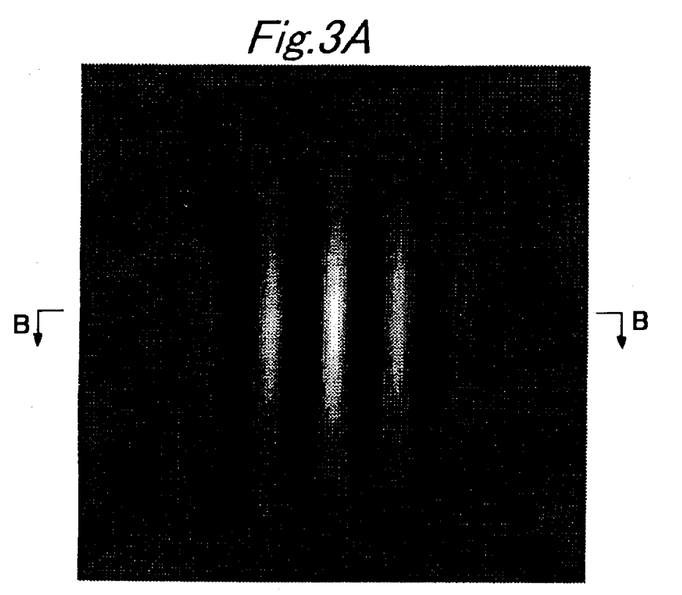
FIGS. 3A and 3B are views explaining a contrast using a contrast sensitivity target.
Figure 3B:
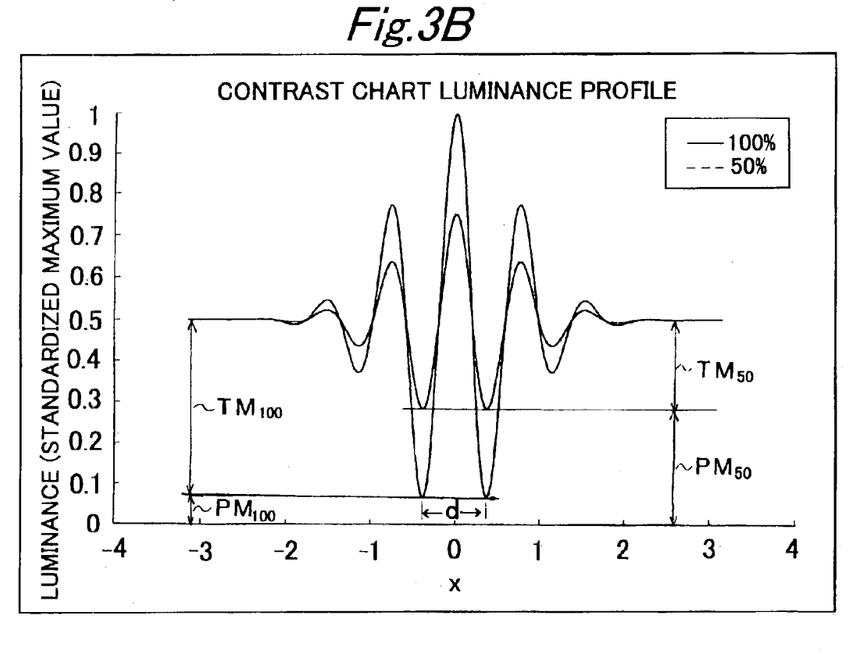

FIG. 3 is views for explaining a contrast using a contrast sensitivity target, in which (A) is a plan view of a Gabor stimulus thrown on the anterior segment of a subject, (B) illustrates the luminance profile of the contrast chart in the direction of B—B in (A). The peak interval "d" of the luminance profile corresponds to the spatial frequency. When the contrast is 100%, since the luminance amplitude of a test target $TM_{100}$ using the Gabor stimulus is large, the luminance of a pedestal target $PM_{100}$ is about 0.08, which is the minimum value of the Gabor stimulus. When the contrast is 50%, since the luminance amplitude of the test target $TM_{50}$ using the Gabor stimulus is smaller than that of the test target $TM_{100}$, the luminance of a pedestal target $PM_{50}$ is about 0.28, which is the minimum value of the Gabor stimulus.

Namely, in a plan view of a Gabor stimulus, the luminance amplitude of the test target varies depending upon the contrast. Thus, a pedestal target having a transmissivity according to the luminance amplitude of the Gabor stimulus must be selected so that the contrast sensitivity targets may have the same brightness. Therefore, the central processing unit 300 drives the target exchanging rotary motors 113 and 133 to obtain a suitable combination of targets on the targets plates 114 and 134. The central processing unit may be able to adjust the quantity of light of the light sources 111 and 131 or the trasnmissivities of the ND filters 115 and 185 to equalize the brightness of the contrast sensitivity targets.

Description will be next made of the method for measuring the contrast sensitivity using data on optical characteristics of the eye to be examined according to the present invention. FIG. 4 is a flowchart for explaining the method for measuring the contrast sensitivity using the optical characteristic data of the eye to be examined. When the measurement of the contrast sensitivity is started (S100), the clinical technologist or ophthalmologist measures the optical characteristics of the eye such as the wavefront aberration with a wavefront sensor 500 (S102). Then, the clinical technologist or ophthalmologist inputs the name of the subject and which one is the eye into the central processing unit 300 (S104).

The contrast target data determination part 320 calculates the modulation transfer function (MTF) using the result of the measurement by the wavefront sensor 500 (S106). Then, the contrast target data determination part 320 predicts the contrast sensitivity of the eye to be examined using the modulation transfer function MTF (S108). The steps S106 and S108 will be described in detail later with reference to FIG. 10 and FIG. 11. The contrast target data determination part 320 then sets a contrast which is higher than the predicted contrast sensitivity by 0.1 dB as an initial value of the contrast sensitivity at each spatial frequency (S110). Then, a certain period of time, one minute, for example, is allowed to pass until the subject gets adapted to the brightness (S112). Preferably, the display part 600 is adapted to display the start and the end of this adaptation time.

The contrast target display control part 330 measures the contrast luminance threshold value at a spatial frequency of 3 cpd (cycles/deg) by, for example, an up-down method (S114). The up-down method is one of psychological measurement methods. The up-down method is a forced choice method in which a target with contrast and a target without contrast are simultaneously displayed once and the subject responses the position where there is a Gabor stimulus. In one display of the contrast sensitivity target, a background is first displayed to the subject, and then a Gabor stimulus is displayed thereto, and the response of the subject is recorded. Then, the central processing unit 300 repeatedly displays a Gabor stimulus to the subject until the measurement is completed. Instead of the up-down method, a method of limits, method of adjustment, constant method, PEST, or QUEST may be employed.

Figure 5A:
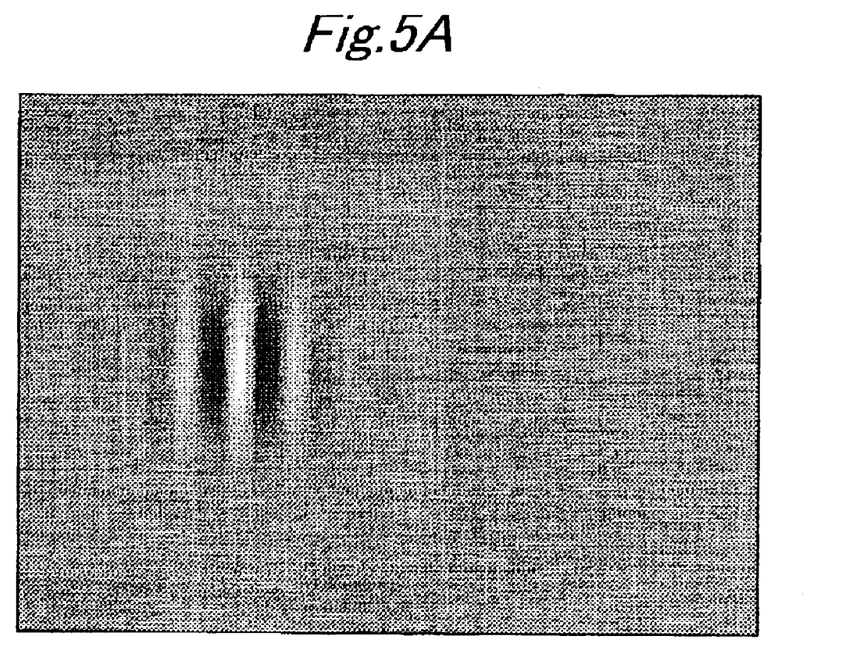
FIGS. 5A and 5B are views explaining a stimulus display pattern for use in an up-down method shown in FIG. 4.
Figure 5B:
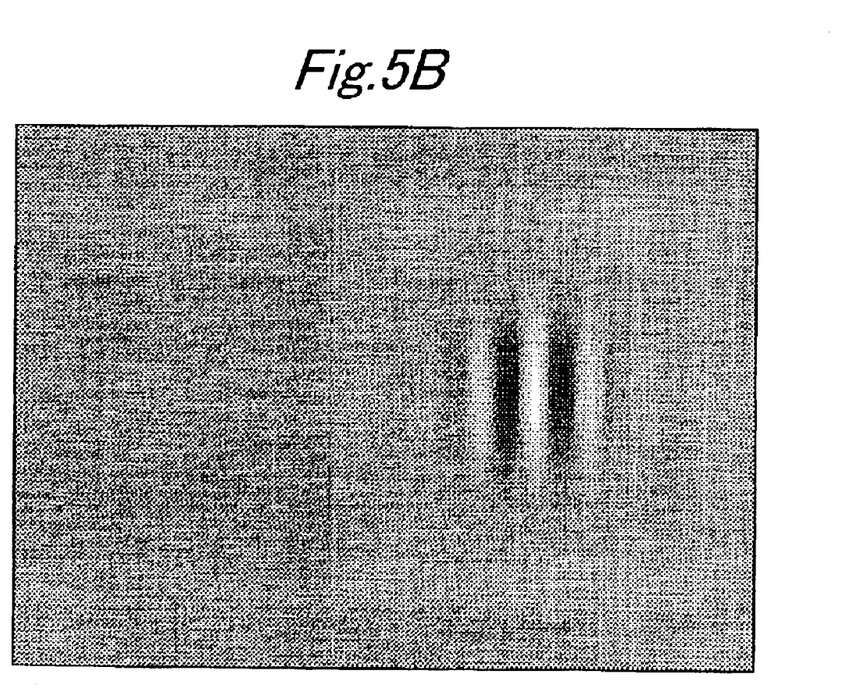

In FIG. 5, displaying examples of targets are shown. In the example shown in FIG. 5(A), a target with high contrast is on the left and a target without contrast is on the right. In the example shown in FIG. 5(B), a target with high contrast is on the right and a target without contrast is on the left. The procedure of the measurement will be described in detail later with reference to FIG. 7.

Next, the contrast target display control part 330 measures the contrast luminance threshold value at a spatial frequency of 6 cpd by, for example, an up-down method (S116). This is followed by the measurement of the contrast luminance threshold value at a spatial frequency of 12 cpd by, for example, an up-down method (S118) and measurement of the contrast luminance threshold value at a spatial frequency of 18 cpd by, for example, an up-down method (S120). Then, from the result of measurement by an up-down method at each spatial frequency, a contrast threshold value is obtained. The reciprocal of a contrast threshold value is taken as the contrast sensitivity (CS) (S122). Then, the response histories in the up-down method at the four spatial frequencies and a contrast sensitivity curve are displayed on the display part 600 (S124). The clinical technologist or ophthalmologist sees the results displayed on the display part 600 and judges whether there is an abnormality at any of the spatial frequencies. Then, when necessary, measurement at one of the spatial frequencies is conducted once again (S126). When the contrast luminance threshold values of the subject are obtained, the central processing unit 300 stores the results such as the target displaying conditions and the responses of the subject in a file (S128), and the measurement of the contrast sensitivity of the subject is completed (S130)

Figure 6:
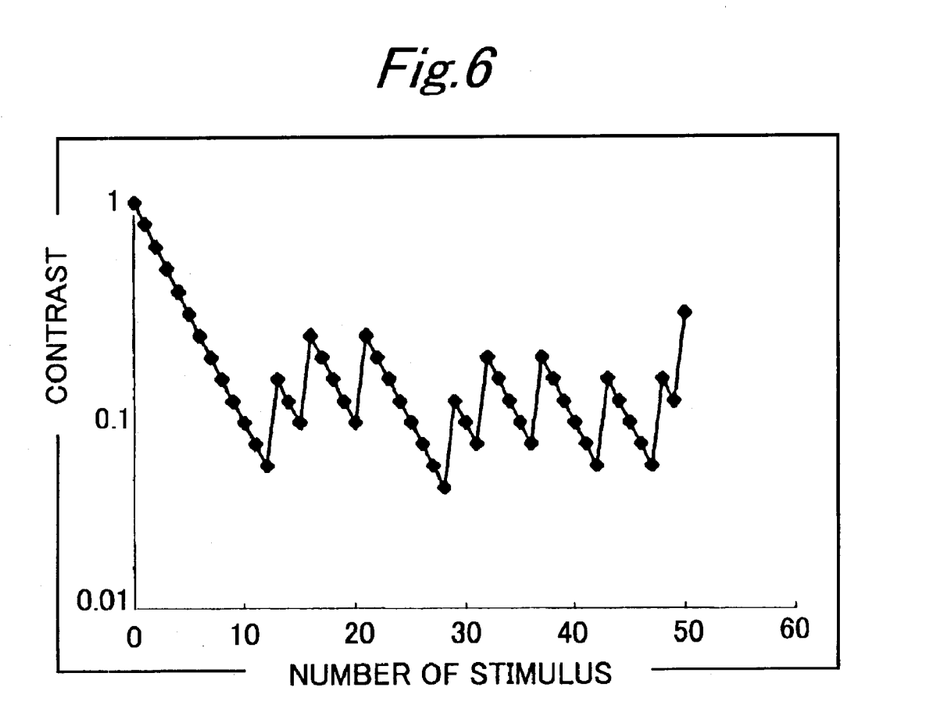
FIG. 6 is a view illustrating an example of changes in contrast in the up-down method shown in FIG. 4.

FIG. 6 is a graph showing an example of the change in contrast in the up-down method shown in FIG. 4, in which the contrast is plotted on the horizontal axis and the number of stimulus on the vertical axis. The measurement is started with a contrast of 100% (considered as 1), and every time the subject responds correctly, the contrast of the stimulus is decreased by 0.1 in logarithm at a time. When the subject responds wrongly, the contrast of the stimulus is increased by four steps. When the subject responds wrongly five times in each ups and downs, the measurement is completed. The contrast threshold value of the subject is the average of the ten contrast threshold values at which the subject responded wrongly, for example 0.06 ($=10^{-1.2}$). The contrast sensitivity of the subject is the reciprocal of the contrast threshold value.

Figure 7:
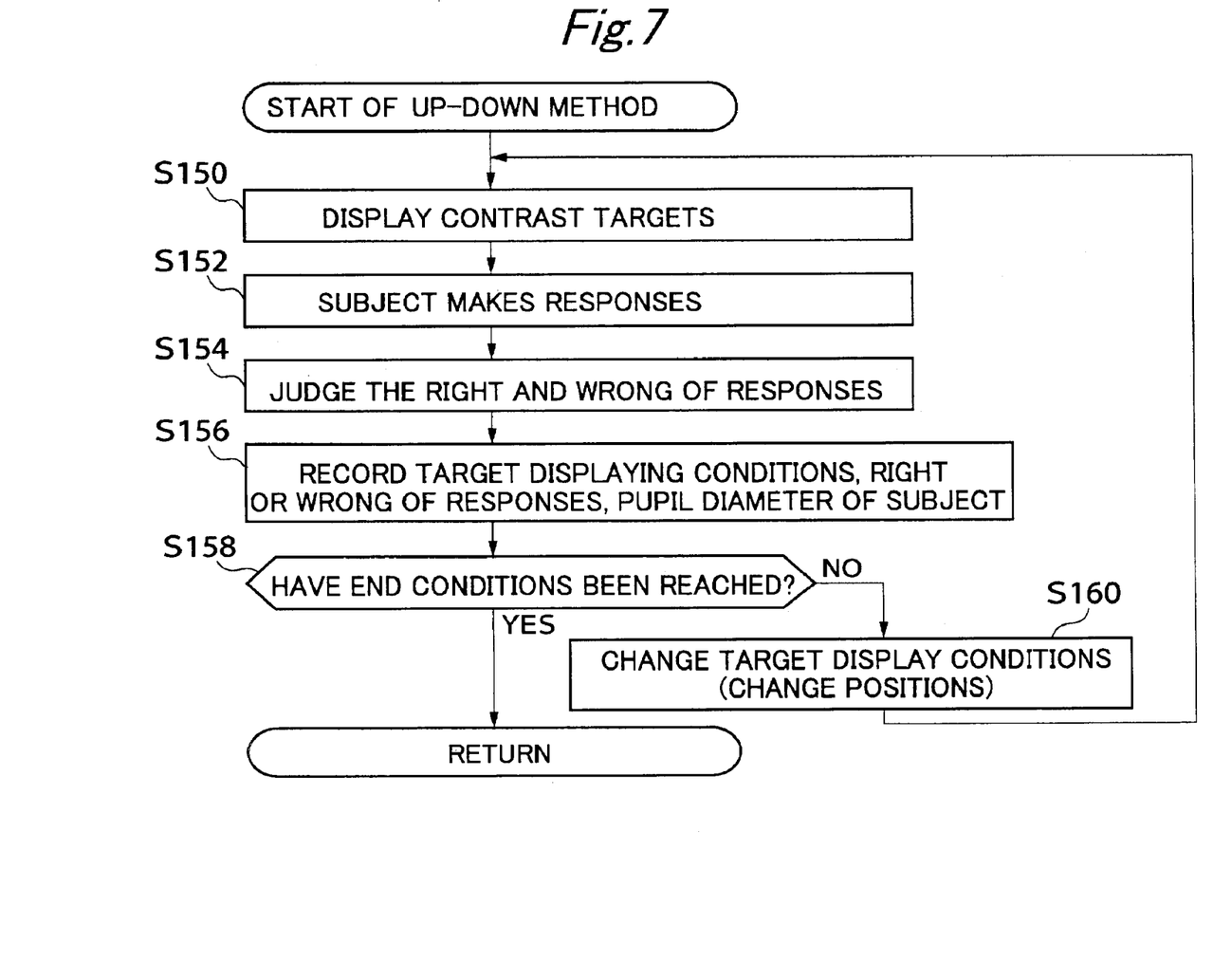
FIG. 7 is a flowchart showing an example of the measurement procedure by an up-down method in which a contrast threshold value is increased and decreased.
Figure 8A:
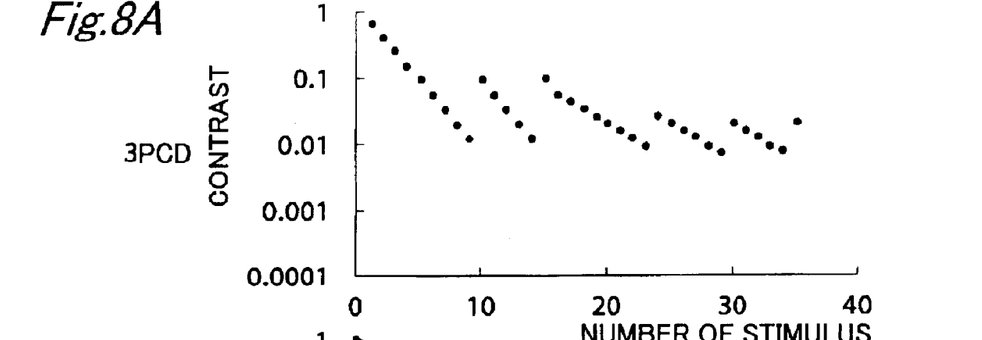
FIGS. 8A–8D are views illustrating an example of the histories of responds of a subject to contrast sensitivity targets with various spatial frequencies.
Figure 8B:
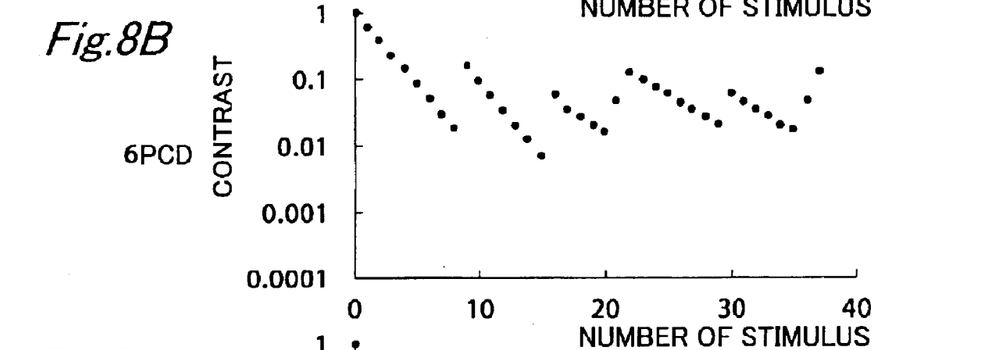
Figure 8C:
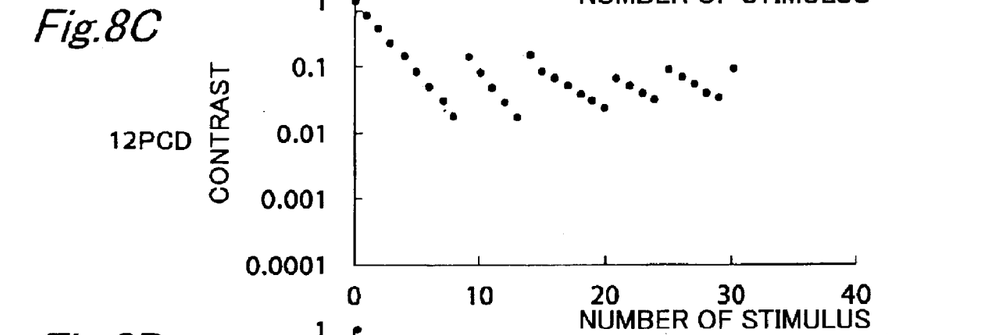
Figure 8D:
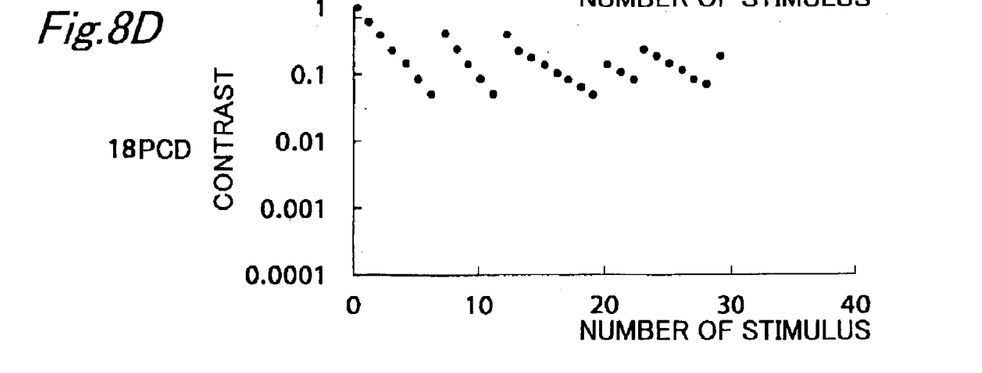

FIG. 7 is a flowchart showing an example of the measurement procedure according to the up-down method. At first, the contrast target display control part 330 displays contrast sensitivity targets each having a predetermined spatial frequency to a subject (S150). At this time, the pupil data measurement part 200 preferably measures the pupil diameter of the subject. Then, the subject makes responses to the displayed contrast sensitivity targets (S152). When the contrast sensitivity targets are displayed by an up-down method, since the display of the stimulus is made according to a two alternative forced choice (2AFC) method, the subject answers the position where there is a Gabor stimulus. The subject may make responses using a subject response device such as a mouse or with voice. The clinical technologist or the central processing unit 300 compares the test targets displayed by the test target display control part 120 and the responses of the subject and judges whether the responses are right or wrong (S154). Then, the central processing unit 300 records the target displaying conditions, the right or wrong of the responses, the pupil diameter of the subject and so forth (S156) The clinical technologist or the central processing unit 300 judges whether the number of times of display of the test targets reaches the end reference number, for example, the number of time of switches from a correct respond to a wrong respond and switches from a correct respond to a wrong respond respectively reach 5 as shown in FIG. 6 (S158). When the number of the shifts has not reached the reference number, the target display conditions are changed (S160) and the process goes back to Step S150.

When the number of display of the test targets has reaches the reference number (S158), the process returns to the start. As above, the process is repeated until the measurement at predetermined spatial frequencies, for example 3, 6, 12 and 18 [cycles/deg], are completed. The time for which a contrast sensitivity target is displayed is 1 to 3 seconds, preferably 2 seconds from a clinical point of view. The results obtained in the contrast measurement according to the up-down method may be analyzed by probit analysis, which is one of statistical analysis methods, after being classified into, for example, 5 contrast levels. By probit analysis, the average s0 and dispersion ό of the contrast thresholds can be obtained.

FIG. 8 is views illustrating an example of the histories of responses of a subject to contrast sensitivity targets with various spatial frequencies, in which (A) (B) (C) and (D) show the cases of grid patterns of a special frequency of 3 cpd ([cycles/deg]), 6 cpd, 12 cpd and 18 cpd, respectively. The history of the responses of the subject at each spatial frequency exhibits a similar pattern to that in the contrast measurement shown in FIG. 6.

Figure 9:
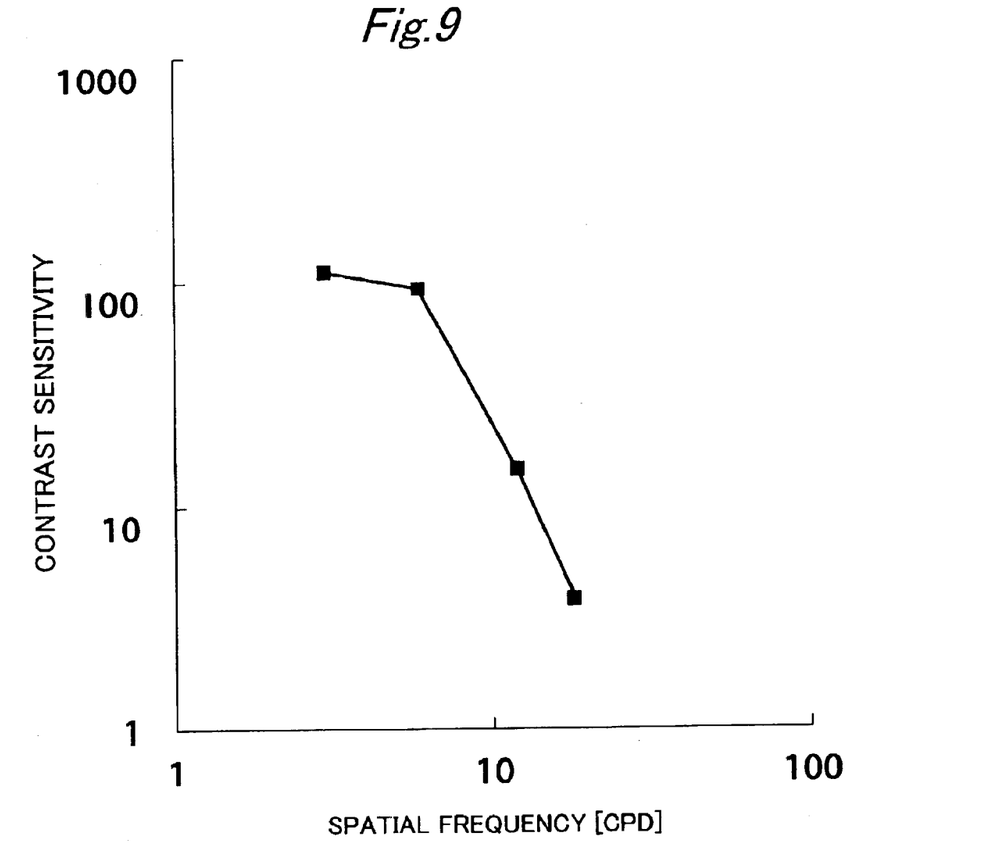
FIG. 9 is a graph showing the relation between the contrast sensitivity and the spatial frequency.

FIG. 9 is a graph showing the relation between the contrast sensitivity and the spatial frequency. Based on the history of the responses of the subject at various spatial frequencies, the contrast threshold values for each spatial frequency are determined. Then, the central processing unit 300 calculates the reciprocals of the contrast threshold values to obtain the contrast sensitivities. In general, the contrast sensitivity of a subject takes the maximum value when the spatial frequency is in the range of 3 to 6 cpd and tends to decrease gradually when the spatial frequency increases to 10 cpd or higher. When the subject has an abnormal value at some spatial frequencies as compared with a standard pattern of the contrast sensitivity to the spatial frequency, there is a possibility that the subject has a lesion in the pupil or optic nerves. Thus, the measurement of contrast sensitivity is suitable as an optical examination.

Figure 10:
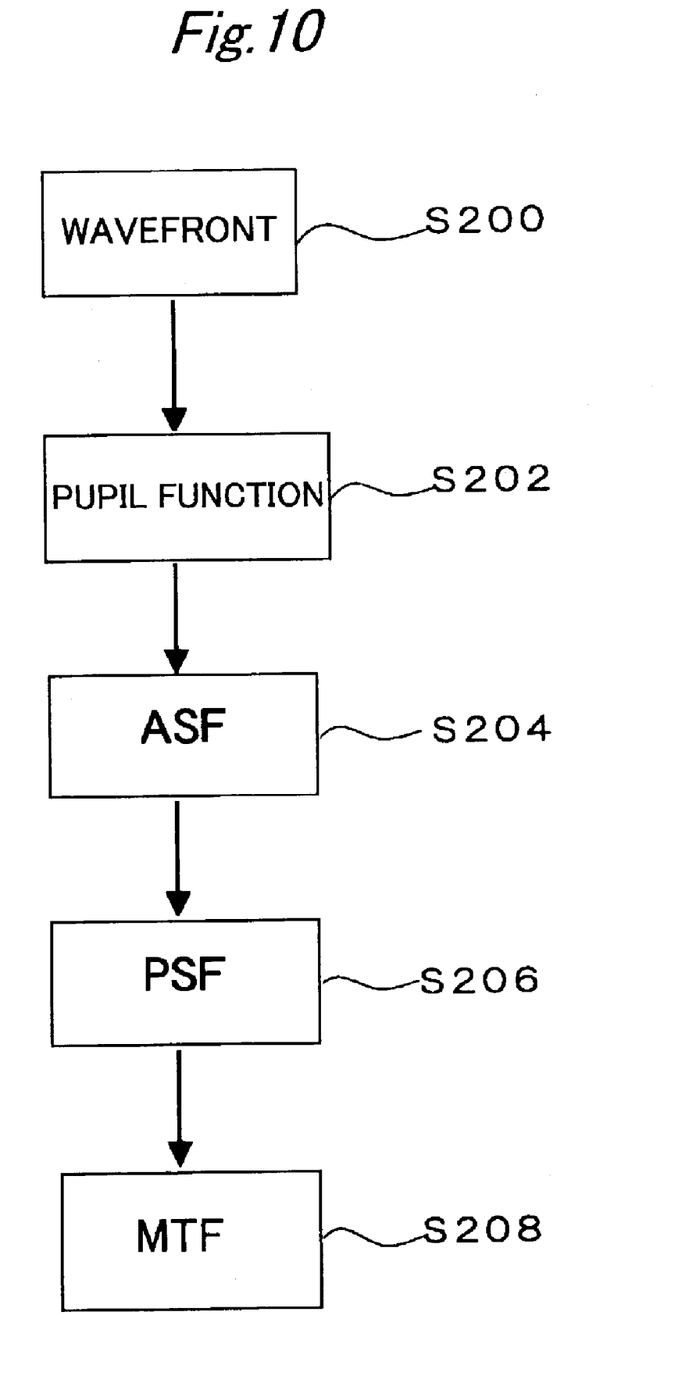
FIG. 10 is a view for explaining the procedure of obtaining a modulation transfer function from a measurement of a wavefront sensor.

FIG. 10 is a flowchart for explaining the procedure of obtaining a modulation transfer function MTF from the measurement by the wavefront sensor. The wavefront toward the pupil of the subject is measured with, for example, a shack-Hartman wavefront sensor 500 (S200). The wavefront W(x, y) measured by the wavefront sensor 500 is converted to a pupil function H(x, y) by the following equation (S202). At this time, the wavefront W(x, y) is assumed to be expressed using the center wavelength of visible light as a unit.

$$H(x, y) = \exp(-2\pi i W(x, y)) \quad (1)$$

Then, the contrast target data determination part 320 subjects the pupil function H(x, y) to two-dimensional Fourier transformation to obtain a amplitude spread function ASF(x, y) (S204).

$$ASF(x, y) = FFT2(H(x, y)) \quad (2)$$

The ASF is an abbreviation of "amplitude spread function". Then, the contrast target data determination part 320 squares the amplitude spread function ASF(x, y) to obtain a point spread function PSF(x, y) (S206).

$$PSF(x, y) = |ASF(x, y)|^2 \quad (3)$$

The PSF is an abbreviation of "point spread function". The contrast target data determination part 320 obtains the modulation transfer function MTF(x, y) by subjecting the point spread function PSF(x, y) to Fourier transformation (S208).

When optical characteristic data of the eye to be examined such as the modulation transfer function have been obtained from the measurement by the wavefront sensor 500 or the like, the modulation transfer function MTF of the optical nerve system can be calculated by the following equation.

$$M_{lat}(u) = \frac{k m_n M_{opt}(u)}{m_t} \quad (4)$$

where $M_{lat}$ is the modulation transfer function MTF of the subject optical nerve system, $M_{opt}$ is the modulation transfer function MTF of the optical system, $m_n$ is the contrast of the noise in the optical nerve system, $m_t$ is the contrast of the stimulus, and k (=s0/ό) is a value obtained by dividing the average s0 of the contrast thresholds by the dispersion thereof. The contrast target data determination part 320 calculates the equation (4) to obtain the modulation transfer function MTF of the optical nerve system.

Figure 11A:
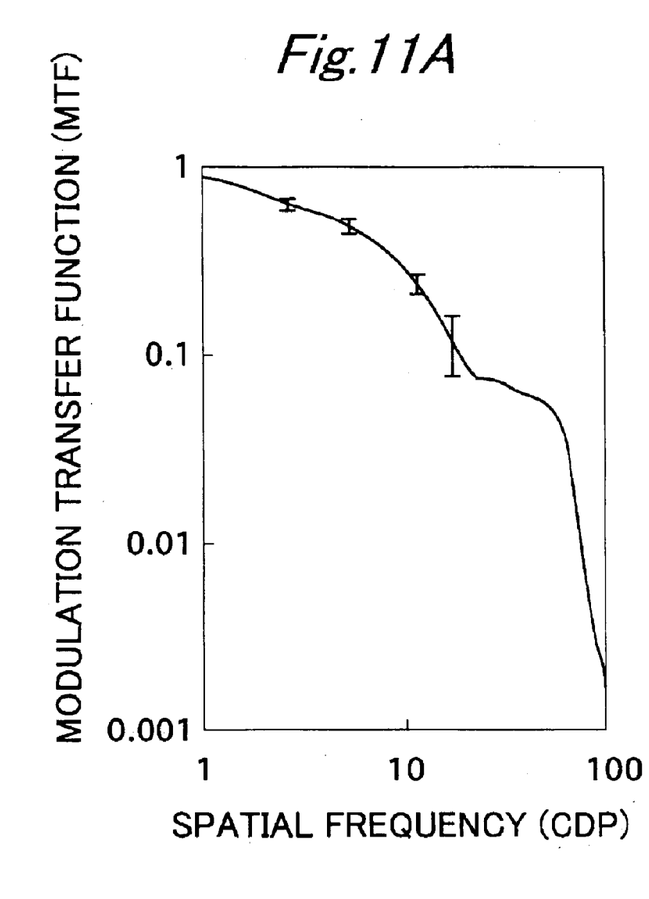
FIGS. 11A and 11B are views explaining a case of making a comparison of a modulation transfer function calculated from wavefront information obtained by the wavefront sensor with a result of measurement of contrast sensitivity on a subject.
Figure 11B:
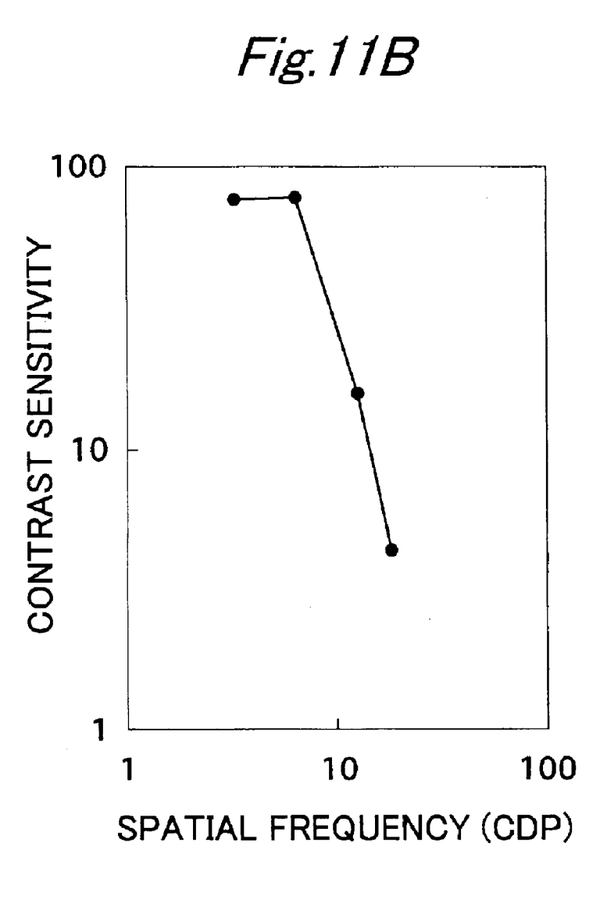

FIG. 11 is views for explaining a case of making a comparison between the modulation transfer function MTF calculated from the wavefront information obtained by the wavefront sensor 500 and results of the contrast measurement of a subject. Since the modulation transfer function MTF has been calculated from the subject wavefront information obtained by the wavefront sensor 500, the contrast target data determination part 320 can obtain the contrast sensitivity CS by the equation (5). Also, the contrast target data determination part 320 can determine the maximum luminance $I_{max}$ and the minimum luminance $I_{min}$ of the targets using the average luminance thereof.

$$MTF = \frac{1}{CS} = \frac{I_{Max} - I_{Min}}{I_{Max} + I_{Min}} \quad (5)$$

As above, the initial value of the contrast sensitivity target for measurement of the contrast sensitivity is obtained from the wavefront information of the eye to be examined. Also, when the correspondence relation between the wavefront information of eye to be examined and the measurement of contrast sensitivity is stored in a data base, predictive values of the contrast sensitivity can be obtained for each spatial frequency from the wavefront information of the eye to be examined. On the other hand, the results of the contrast measurement of the subject obtained from the central processing unit are displayed on the display part 600 together with the predictive values. Then, the clinical technologist or ophthalmologist can easily judge whether the subject has a lesion in the eye or not with reference to the comparison of the predictive values and the measurements, as shown in FIG. 11.

In the above embodiment, an example in which the device is configured to measure the contrast sensitivity of an eye of a subject at a time is shown. However, the device may be configured to measure the contrast sensitivity of both eyes of a subject simultaneously to evaluate the binocular function of the subject.

Also, in the first embodiment, an example in which the test targets are sent from the first illumination optical system 110 and the pedestal targets are sent from the second illumination optical system 130 is shown. However, the target plates 114 and 134 may be exchanged so that the pedestal targets and the test targets are sent from the first illumination optical system 110 and the second illumination optical system 130, respectively. Also, the contrasts of the pedestal targets and the test targets, which are changed using the target plate 114 in the above embodiment, may be changed by varying the quantity of light of the light sources 131 and 111 or by varying the transmissivities (density) of the ND filters 135 and 115.

In a clinical site such as a hospital or a department of drivers license, a visual function inspecting device like a contrast sensitivity measuring device is generally used together with an aberration meter or a wavefront sensor for examining the eye optical system. Thus, it is very effective and innovative in a clinical site to facilitate the measurement of contrast sensitivity with a contrast sensitivity measuring device and to systemize the measurement of contrast sensitivity with related objective measurements such as measurements with an aberration meter and a wavefront sensor. In addition, some aberration meters and wavefront sensors have a function of a refractometer or an autorefractometer, so that combining such an aberration meter or a wavefront sensor with a visual function inspecting device and a horopter further facilitates the work in a clinical site and makes it possible to perform an detailed examination which was not able to be practiced before.

In the above first embodiment, an example in which spatial frequencies of 3, 6, 12, and 18 [cycles/deg] are used as the spatial frequencies of the contrast sensitivity targets displayed by the contrast target display control part 300, but the present invention is not limited thereto. For example, when the optical characteristic data of the eye to be examined indicate that the aberration thereof is large, the contrast target data determination part 320 may shift the spatial frequencies of the contrast sensitivity targets to the lower side to perform measurements at spatial frequencies of 1, 3, 6, and 12 [cycles/deg], for example.

As has been described above, the contrast sensitivity measuring device of the present invention comprises a contrast target display part for displaying contrast targets for contrast sensitivity test, a contrast target data determination part for determining contrast targets to be displayed on the contrast target display part according to data on optical characteristics of an eye of a subject to be examined, a contrast target display control part for instructing the contrast target display part to display contrast targets based on contrast target data created in the contrast target data determination part according to a predetermined procedure, and a display part for displaying the results of contrast measurement of the subject using data on a history of responses of the subject to displayed contrast targets. Thus, by organically combining optical characteristic data of an eye to be examined such as a wavefront and the contrast target display part using the contrast target data determination part and the contrast target display control part, an initial value of the contrast sensitivity measurement can be determined from the optical characteristic data of the eye to be examined, so that the time for measurement can be shortened.

Also, since the optical characteristic data of the eye to be examined is a modulation transfer function calculated from wavefront information obtained by a wavefront sensor in a spatial frequency region including spatial frequencies displayed on the contrast target display part, the clinical technologist or ophthalmologist can easily compare the modulation transfer function MTF calculated from the wavefront with results of a subjective contrast sensitivity test.

What is claimed is:

1. A contrast sensitivity measuring device comprising:
    a contrast target display part for displaying contrast targets;
    a contrast target data determination part for determining contrast targets, to be displayed on said contrast target display part, according to data on ocular aberration of an eye of a subject to be examined;
    a contrast target display control part for instructing said contrast target display part to display contrast targets based on contrast target data created in said contrast target data determination part according to a predetermined procedure; and
    a display part for displaying the results of contrast measurement of said subject using data on a history of responses of said subject to displayed contrast targets.

2. A contrast sensitivity measuring device as claimed in claim 1, wherein said contrast target determination part is adapted to determine said contrast targets, to be displayed on said contrast target display part, based on the results of the contrast measurement which has been already performed on said subject in addition to said data on ocular aberration of said eye to be examined.

3. A contrast sensitivity measuring device as claimed in claim 2, wherein said contrast target determination part is configured to determine at least one of an initial value of said contrast targets to be displayed and a changing rate of said contrast targets to be displayed based on said data ocular aberration of said eye to be examined.

4. A contrast sensitivity measuring device as claimed in claim 3, wherein said display part is adapted to display said results of the contrast measurement of said subject such that said data on ocular aberration of said subject are reflected in said results.

5. A contrast sensitivity measuring device as claimed in claim 4, wherein said display part is configured to perform, for the reflection of said data on ocular aberration of said subject, at least one of display of a permissive range by which said result of measurement of contrast of said subject can be judged to be normal or not, display of a measurement area corresponding to an abnormal eye with respect to said result of measurement of contrast of said subject, and display of the fact that said result of measurement of contrast of said subject falls out of a permissive range.

6. A contrast sensitivity measuring device as claimed in claim 5, wherein said data on ocular aberration of said eye to be examined is a modulation transfer function calculated from wavefront information obtained by a wavefront sensor in a spatial frequency region including spatial frequencies displayed on said contrast target display part.

7. A contrast sensitivity measuring device as claimed in claim 4, wherein said data on ocular aberration of said eye to be examined is a modulation transfer function calculated from wavefront information obtained by a wavefront sensor in a spatial frequency region including spatial frequencies displayed on said contrast target display part.

8. A contrast sensitivity measuring device as claimed in claim 1, wherein said contrast target determination part is configured to determine at least one of an initial value of said contrast targets to be displayed and a changing rate of said contrast targets to be displayed based on said data on ocular aberration of said eye to be examined.

9. A contrast sensitivity measuring device as claimed in claim 8, wherein said display part is adapted to display said results of the contrast measurement of said subject such that said data on ocular aberration of said subject are reflected in said results.

10. A contrast sensitivity measuring device as claimed in claim 9, wherein said display part is configured to perform, for the reflection of said data on ocular aberration of said subject, at least one of display of a permissive range by which said result of measurement of contrast of said subject can be judged to be normal or not, display of a measurement area corresponding to an abnormal eye with respect to said result of measurement of contrast of said subject, and display of the fact that said result of measurement of contrast of said subject falls out of a permissive range.

11. A contrast sensitivity measuring device as claimed in claim 10, wherein said data on ocular aberration of said eye to be examined is a modulation transfer function calculated from wavefront information obtained by a wavefront sensor in a spatial frequency region including spatial frequencies displayed on said contrast target display part.

12. A contrast sensitivity measuring device as claimed in claim 9, wherein said data on ocular aberration of said eye to be examined is a modulation transfer function calculated from wavefront information obtained by a wavefront sensor in a spatial frequency region including spatial frequencies displayed on said contrast target display part.

13. A contrast sensitivity measuring device as claimed in claims 1, wherein said display part is adapted to display said results of the contrast measurement of said subject such that said data on ocular aberration of said subject are reflected in said results.

14. A contrast sensitivity measuring device as claimed in claim 13, wherein said display part is configured to perform, for the reflection of said data on ocular aberration of said subject, at least one of display of a permissive range by which said result of measurement of contrast of said subject can be judged to be normal or not, display of a measurement area corresponding to an abnormal eye with respect to said result of measurement of contrast of said subject, and display of the fact that said result of measurement of contrast of said subject falls out of a permissive range.

15. A contrast sensitivity measuring device as claimed in claim 14, wherein said data on ocular aberration of said eye to be examined is a modulation transfer function calculated from wavefront information obtained by a wavefront sensor in a spatial frequency region including spatial frequencies displayed on said contrast target display part.

16. A contrast sensitivity measuring device as claimed in claim 13, wherein said data on ocular aberration of said eye to be examined is a modulation transfer function calculated from wavefront information obtained by a wavefront sensor in a spatial frequency region including spatial frequencies displayed on said contrast target display part.

17. A contrast sensitivity measuring device as claimed in claim 1, wherein said data on ocular aberration of said eye to be examined is a modulation transfer function calculated from wavefront information obtained by a wavefront sensor in a spatial frequency region including spatial frequencies displayed on said contrast target display part.

18. A contrast sensitivity measuring method comprising the steps of:
- determining contrast targets to be displayed on a contrast target display part, according to data on ocular aberration of an eye of a subject to be examined,
- displaying contrast targets on said contrast target display part based on contrast target data created in a contrast target data determination part according to a predetermined procedure; and
- displaying the result of measurement of a contrast of a subject using data on a history of responses of said subject to displayed contrast targets.

* * * * *